US011267965B2

(12) United States Patent
Liu et al.

(10) Patent No.: US 11,267,965 B2
(45) Date of Patent: Mar. 8, 2022

(54) POLYMERIC MATERIALS FOR BIOMEDICAL APPLICATIONS

(71) Applicants: Aleo BME, Inc., State College, PA (US); The Penn State Research Foundation, University Park, PA (US)

(72) Inventors: Chao Liu, State College, PA (US); Jian Yang, University Park, PA (US)

(73) Assignees: Aleo BME, Inc., State College, PA (US); The Penn State Research Foundation, University Park, PA (US)

( * ) Notice: Subject to any disclaimer, the term of this patent is extended or adjusted under 35 U.S.C. 154(b) by 247 days.

(21) Appl. No.: 15/779,623

(22) PCT Filed: Nov. 29, 2016

(86) PCT No.: PCT/US2016/064018
§ 371 (c)(1),
(2) Date: May 29, 2018

(87) PCT Pub. No.: WO2017/095816
PCT Pub. Date: Jun. 8, 2017

(65) Prior Publication Data
US 2018/0340063 A1     Nov. 29, 2018

Related U.S. Application Data

(60) Provisional application No. 62/260,752, filed on Nov. 30, 2015.

(51) Int. Cl.
| | | |
|---|---|---|
| *C08L 67/02* | (2006.01) | |
| *C08L 67/04* | (2006.01) | |
| *C08L 67/06* | (2006.01) | |
| *C08L 71/00* | (2006.01) | |
| *C08L 75/04* | (2006.01) | |
| *A61L 27/18* | (2006.01) | |
| *A61L 15/26* | (2006.01) | |
| *C08G 18/48* | (2006.01) | |
| *C08G 18/10* | (2006.01) | |
| *C08G 18/73* | (2006.01) | |
| *C08G 18/42* | (2006.01) | |
| *C08G 18/24* | (2006.01) | |

(52) U.S. Cl.
CPC .............. *C08L 67/02* (2013.01); *A61L 15/26* (2013.01); *A61L 27/18* (2013.01); *C08G 18/10* (2013.01); *C08G 18/246* (2013.01); *C08G 18/4236* (2013.01); *C08G 18/4277* (2013.01); *C08G 18/4833* (2013.01); *C08G 18/73* (2013.01); *C08L 67/04* (2013.01); *C08L 67/06* (2013.01); *C08L 71/00* (2013.01); *C08L 75/04* (2013.01); *A61L 2430/02* (2013.01); *A61L 2430/32* (2013.01); *C08L 2201/06* (2013.01); *C08L 2203/02* (2013.01)

(58) Field of Classification Search
CPC ...... C08G 18/10; C08G 18/4833; C08L 75/04; C08L 2201/06; C08L 2203/02; C08L 67/02; C08L 67/04; C08L 67/06; C08L 71/00
See application file for complete search history.

(56) References Cited

U.S. PATENT DOCUMENTS

| | | | |
|---|---|---|---|
| 7,674,416 B2 | 3/2010 | Hong et al. | |
| 2009/0093565 A1 | 4/2009 | Yang et al. | |
| 2009/0175921 A1* | 7/2009 | Gunatillake | C08G 18/4277 424/423 |
| 2009/0275872 A1* | 11/2009 | Addison | A61K 31/7024 602/46 |
| 2009/0299466 A1 | 12/2009 | Hezi-Yamit | |
| 2014/0193356 A1* | 7/2014 | Yang | A61P 19/08 424/78.17 |

FOREIGN PATENT DOCUMENTS

| | | | | |
|---|---|---|---|---|
| CN | 103751148 | * | 4/2014 | ............... A61K 9/51 |
| CN | 103751148 A | | 4/2014 | |
| CN | 104470904 A | | 3/2015 | |
| CN | 104937096 A | | 9/2015 | |
| GB | 2394418 A | | 4/2004 | |
| JP | 2009093565 A | | 4/2009 | |
| JP | 2015513591 A | | 5/2015 | |
| WO | 2014107501 A1 | | 7/2014 | |
| WO | 2015035020 A1 | | 3/2015 | |

OTHER PUBLICATIONS

Wang et al. (Polym Chem. 2011, 2, 601-607).*
Li et al. (Journal of Nutritional Biochemistry 24 (2013) 1295-1301 (Year: 2013).*
International Preliminary Report on Patentability issued in Application No. PCT/US2016/064018 dated Jun. 14, 2018.
International Search Report issued in Application No. PCT/US2016/064018 dated Apr. 4, 2017.
Chinese application No. 201680069935.2; Office Action dated Mar. 26, 2021, 11 pages.
Office Action dated Apr. 13, 2021, corresponding to EP 16871362.6, 4 pages.
Office Action dated Aug. 3, 2021, corresponding to JP 2018-547859, 10 pages.
Zhang, Siyan et al., Synthesis and Evaluation of Clickable Block Copolymers for Targeted Nanoparticle Drug Delivery, Molecular Pharmaceutics, 2012, pp. 2228-2236.
Smith, David A. et al., Homocysteine-Lowering by B Vitamins Slows the Rate of Accelerated Brain Atrophy in Mild Cognitive Impairment: A Randomized Controlled Trial, PLOS One, Sep. 2010, vol. 5, Issue 9, e12244, pp. 1-10.

(Continued)

*Primary Examiner* — Anna R Falkowitz
(74) *Attorney, Agent, or Firm* — Nexsen Pruet, PLLC

(57) ABSTRACT

Crosslinked biodegradable block polyurethane copolymers prepared from a plurality of biodegradable polymers or oligomers linked together via urethane bonds and crosslinked via a citrate ester are disclosed. Such copolymers can include folic acid and fabricated into medical devices such as a nerve growth conduit and locally deliver folic acid to a site of injury such as a PNS injury site.

13 Claims, 10 Drawing Sheets

(56) References Cited

OTHER PUBLICATIONS

Couto, Mafalda R. et al., The Effect of Oxidative Stress Upon the Intestinal Uptake of Folic Acid: In Vitro Studies with Caco-2 cells, Cell Biol Toxicol (2012) 28, pp. 369-381.

Iskandar, Bermans J. et al., Folate Regulation of Axonal Regeneration in the Rodent Central Nervous System Through DNA Methylation, The Journal of Clinical Investigation, vol. 120, No. 5, May 2010, pp. 1603-1616.

Luo, Suhui et al., Folic Acid Acts Through DNA Methyltransferases to Induce the Differentiation of Neural Stem Cells into Neurons, Cell Biochem Biophys (2013), 66, pp. 559-566.

Li, Wen et al., DNA Methyitransferase Mediates Dose-Dependent Stimulation of Neural Stem Cell Proliferation by Folate, Journal of Nutritional Biochemistry 24, 2013, pp. 1295-1301.

Liu, Huan et al., Folic Acid Supplementation Stimulates Notch Signaling and Cell Proliferation in Embryonic Neural Stem Cells, J. Clin. Biochem, Nutr., 47, Sep. 2010, pp. 174-180.

Kageyama, Ryoichiro et al., Roles of Hes Genes in Neural Development, Develop. Growth Differ. (2008), 50, pp. S97-S103.

De la Pompa, Jose Luis et al., Conservation of the Notch Signalling Pathway in Mammalian Neurogenesis, Development 124, (1997), pp. 1139-1148, printed in Great Britain ©The Company of Biologists Limited 1997.

Crider, Krista S. et al., Folate and DNA Methylation: A Review of Molecular Mechanisms and the Evidence for Folate's Role1,2, American Society for Nutrition, Adv. Nutr. 3, pp. 21-38, 2012, doi:10.3945/an.111.000992.

Kalmbach, Renee D. et al., Circulating Folic Acid in Plasma: Relation to Folic Acid Fortification, Published in final edited form as: Am J Clin Nutr. Sep. 2008, 88(3), pp. 763-768.

Harma, Md, Ahmet et al., Effects of Intraperitoneally Administered Folic Acid on the Healing of Repaired Tibial Nerves in Rats, Journal of Reconstructive Microsurgery, vol. 31, No. 3 (2015), published online Nov. 25, 2014, DOI http://dx.doi.org/10.1055/s-0034-1395414, ISSN 0743-684X, pp. 191-197.

\* cited by examiner $R_1$ and $R_2$ = H
or 
or polymer chain
or polymer chain-OH $R_3$ and $R_4$ = H or polymer chain
or polymer chain-OH R = H
or ⌇≡
or polymer chain

A (POC-FA)

Diol monomers (H1) and  (H2), (I1),  (I2), (I3),  (I4), (I5), and  (I6), wherein $R_{30}$ is -CH$_3$ or -CH$_2$CH$_3$; and X is -NH- or -O-

POLYMERIC MATERIALS FOR BIOMEDICAL APPLICATIONS

CROSS-REFERENCE TO RELATED APPLICATION

This application is a national stage of International Application No. PCT/US2016/064018, filed 29 Nov. 2016, which claims the benefit of U.S. Provisional Application No. 62/260,752 filed 30 Nov. 2015 the entire disclosures of which are hereby incorporated by reference herein.

FIELD

The present disclosure relates to crosslinked biodegradable block polyurethane copolymers and their use in medical devices.

BACKGROUND

Peripheral nerve injury is a serious clinical problem that affects approximately 360,000 people every year in the United States alone. It damages tissues, organs, and the nerves in the peripheral nervous system (PNS), resulting in debilitating long-term pain, paralysis, or limb malfunction. The current gold standard for repair is autografts, but the use of autografts has disadvantages including the need for multiple surgical procedures, morbidity or loss of sensation at the donor site, limited supply of available grafts, and the potential for neuroma formation. Thus, there is a high demand to develop alternative approaches that can match or exceed the performance of autografts.

Nerve guidance conduit (NGC) is one approach to address the challenges of peripheral nerve repair. In current state-of-the-art treatment for nerve trauma, a few biodegradable synthetic nerve repair conduits (NGC) are commercially available for clinical use, i.e., Neurolac® (Polyganics), NeuraGen (Integra LifeSciences), NeuraWrap (Integra Life Sciences), NeuroMend (Collagen Matrix), GEM™ Neurotube (Synovis Micro), Avance® Nerve Graft (AxoGen), NeuroFlex (Collagen Matrix), and Salutunnel (Salumedica). The NGCs are made from biodegradable polymers such as poly(L-lactic acid) (PLLA), poly (D, L-lactic-co-glycolic acid) (PLGA), polycaprolactone (PCL), polyvinyl alcohol (PVA) or collagen. Although these nerve conduits provide an alternative surgical option over autografts, their performance still remains inferior to autografts in the functional recovery of injured nerves, even over short injury gaps. Overall, the currently available synthetic nerve repair conduit products have a suboptimal regenerative capacity and poor functional recovery compared to autograft in treating relatively large nerve gaps (>1 cm in length for rats or >4 cm in length for humans).

Biodegradable polyurethanes (PU) or urethane-doped polyesters have been explored as useful biomaterials due to their excellent mechanical and processing properties and good biocompatibility. Yang et al. described a systematic investigation on the application of a crosslinked urethane-doped biodegradable polyester (CUPE) scaffolds for nerve regeneration. See Tran et al., J Biomed Mater Res A. 2014, 102(8):2793-804: see also U.S. Pat. No. 7,923,486 B2.

In addition, Niu et al., Biomaterials 2014:35:4266-77, disclosed scaffolds from block polyurethanes based on poly-lactic acid (PLA) and polyethylene glycol (PEG) for peripheral nerve regeneration. Li et al., J Biomed Mater Res Part A 2014:102A:685-97, disclose alternating block polyurethanes based on polycaprolactone (PCL) and polyethylene glycol (PEG) as potential nerve regeneration materials.

Moreover, folic acid, a water-soluble vitamin B9, is known to play a role in central nervous system (CNS) development, function, and repair. It is also disclosed as a target for treating tumors. For example, U.S. Pat. No. 7,316,811 discloses multi-arm polypeptide-poly(ethylene glycol) block copolymers as drug delivery vehicles and folic acid as a targeting agent for treating tumors. However, it is believed that local delivery of folic acid to a site of PNS injury has not been disclosed.

Hence, a continuing need exists to provide biodegradable medical devices such as such as nerve repair conduits, tissue scaffolds tarsal and wound dressings.

SUMMARY

Advantages of the present disclosure include crosslinked biodegradable (alternating or random) block polyurethane copolymers and their use in medical devices. Such block copolymers include a plurality of biodegradable polymers or oligomers linked together via urethane bonds. Advantageously, the block copolymers can be crosslinked via a citrate ester.

These and other advantages are satisfied, at least in part, by a crosslinked biodegradable block polyurethane copolymers comprising; a plurality of first blocks formed from a first biodegradable polymer or oligomer, and a plurality of second blocks formed from a second biodegradable polymer or oligomer that differs from the first polymer or oligomer; wherein the first blocks and second blocks are linked via urethane bonds and crosslinked via a citrate ester.

Embodiments of the block copolymer include, individually or in combination, wherein the first or second polymer or oligomer comprises a diol-terminated or diisocyanate-terminated polyester prepared from the reaction product of (i) citric acid, a citrate, or an ester of citric acid with (ii) a polyol and/or (iii) an amine, an amide, an amino acid or a molecule comprising a primary amine moiety, an isocyanate such as a diisocyanate, or a polycarboxylic acid or a functional equivalent thereof, or a catechol-containing species. In some embodiments, the block copolymer incorporated folic acid either physically or covalently.

Another aspect of the present disclosure includes a medical device formed from the block copolymer. Various medical devices can be fabricated from the crosslinked biodegradable block polyurethane copolymers of the present disclosure including nerve repair conduits, tissue scaffolds tarsal and wound dressings, cellular ingrowth, cartilage reconstruction, organ replacement and repair, ligament and tendon repair, bone reconstruction and repair, skin reconstruction and repair, vascular graft, and coronary stents, other soft and hard tissue regeneration and implantable medical devices can also be made from the biomaterials.

Advantageously, the crosslinked biodegradable block polyurethane copolymers of the present disclosure can be fabricated as a luminal structure, such as a nerve growth conduit. The NGCs can be single channeled or multi-channeled, porous and non-porous, tapered and non-tapered and a variable degradation rate depending on location of the conduit.

In certain embodiments, the medical device is formed from one or more crosslinked biodegradable block polyurethane copolymers of the present disclosure incorporating folic acid, e.g., either physically or covalently. Such a medical device can locally deliver folic acid to a site of injury such as a PNS injury site. Hence, an aspect of the present disclosure includes methods for delivering folic acid to an injury site to treat or repair an injury, e.g., a PNS injury, or wound or repair tissue such as a tarsus repair by disposing a medical device formed from one or more crosslinked biodegradable block polyurethane copolymers of the present disclosure incorporating folic acid.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 1A is a scheme for poly(octamethylene citrate)-click-FA (POC-FA); and FIG. 1B is a scheme for folic acid click-conjugated electrically conductive biodegradable photoluminescent polymer (BPLP-aniline tetramer) (BPLP-AT-FA).

DETAILED DESCRIPTION

Figure 1A:
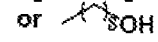
FIGS. 1A and 1B are schemes of syntheses of citrate polymers conjugated with folic acid (FA).
Figure 1A:
Figure 1A:
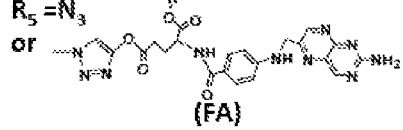
Figure 1A:
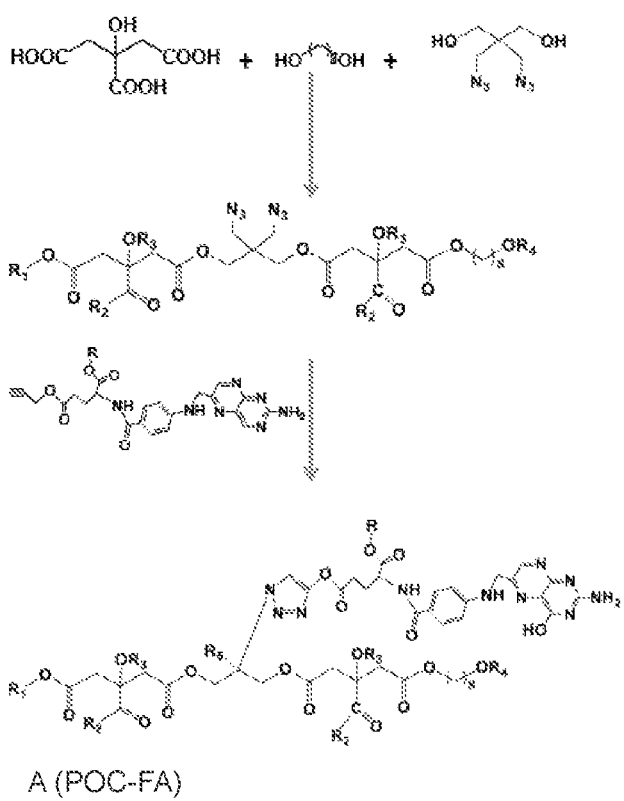

The present disclosure relates to crosslinked biodegradable block polyurethane copolymers that offer synergistic effects of multiple cues, including mechanical, topological, electrical, and biological cues for biodegradable medical devices such as nerve repair conduits, tissue scaffolds tarsal and wound dressings. Other medical devices, such as tissue engineering scaffolds for cellular ingrowth, cartilage reconstruction, organ replacement and repair, ligament and tendon repair, bone reconstruction and repair, skin protectant, skin reconstruction and repair, vascular graft, and coronary stents, other soft and hard tissue regeneration, tissue adhesives and surgical sealants, and implantable medical devices and cosmetic products such as nail polish and second-skin or aesthetic devices can also be made from the biomaterials. The mentioned medical devices and scaffolds can be fabricated using the common methods such as salt leaching, gas-foaming, in-situ forming, freeze-drying, electrospinning, extrusion, molding, casting and even 3-dimensional (3D) printing or additive manufacturing.

In one aspect of the present disclosure, the crosslinked biodegradable material include block polyurethane copolymers include a plurality of first blocks formed from a first biodegradable polymer or oligomer; and a plurality of second blocks formed from a second biodegradable polymer or oligomer that differs from the first polymer or oligomer. The first blocks and second blocks are linked via urethane bonds and crosslinked via a citrate ester. The block copolymer can be an alternating block copolymer comprising alternating first blocks and second blocks; or the block copolymer can be a random block copolymer. The first biodegradable polymer or oligomer and the second biodegradable polymer or oligomer can each have a weight average molecular weight of at least 300, at least 400, or at least 500.

In certain embodiments of the present disclosure, the first or second polymer or oligomer comprises a diol-terminated or diisocyanate-terminated polyester prepared from the reaction product of (i) citric acid, a citrate, or an ester of citric acid with (ii) a diol or a polyol, wherein the citrate has the structure of Formula (I):

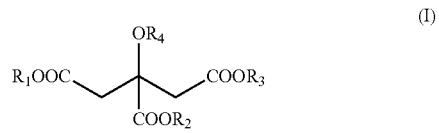

wherein $R_1$, $R_2$, and $R_3$ are independently —H, lower alkyl such as —$CH_3$, —$CH_2CH_3$, or $M^+$; $R_4$ is —H or $M^+$; and $M^+$ is a metal cation. The diol can include other functional groups, e.g., azide or alkyne groups, and the polyol can include a C2-C20 α,ω-n-alkane diol, a poly(ethylene glycol), a poly(propylene glycol), for example.

The citrate polyester can also be prepared from additional condensation monomers. For example, a diol-terminated or diisocyanate-terminated polyester prepared from the reaction product of (i) citric acid, a citrate, or an ester of citric acid with (ii) a polyol, and (iii) an amine, an amide, an amino acid or a molecule comprising a primary amine moiety, an isocyanate such as a diisocyanate, or a polycarboxylic acid or a functional equivalent thereof, or a catechol-containing species. The amino acid can include an alpha-amino acid or an alkyl-substituted alpha-amino acid: the polycarboxylic acid or functional equivalent thereof can include maleic acid, maleic anhydride, fumaric acid, or fumaryl chloride; and the catechol-containing species can include dopamine, L-3,4-dihydroxyphenylalanine, D-3,4-dihydroxyphenylalanine, or 3,4-dihydroxyhydrocinnamic acid, for example.

In some embodiments, the citrate polyester can also be prepared from one or more monomers of Formula (A) with: (i) one or more monomers of Formula (B1) or (B2); (ii) one or more monomers of Formula (B1) or (B2), and one or more monomers of Formula (C); (iii) one or more monomers of Formula (B1) or (B2), and one or more monomers of Formula (D1) or (D2); (iv) one or more monomers of Formula (B1), (B2) or (B3), and one or more monomers of Formula (E); (v) one or more monomers of Formula (B1) or (B2), and one or more monomers of Formula (F); (vi) one or more monomers of Formula (B4), (B5), or (B6); or (vii) one or more monomers of Formula (B4), (B5) or (B6), and one or more monomers comprising one or more alkyne moieties or one or more azide moieties, wherein the Formula A, B1-B6, C, D, E, F have the following structures:

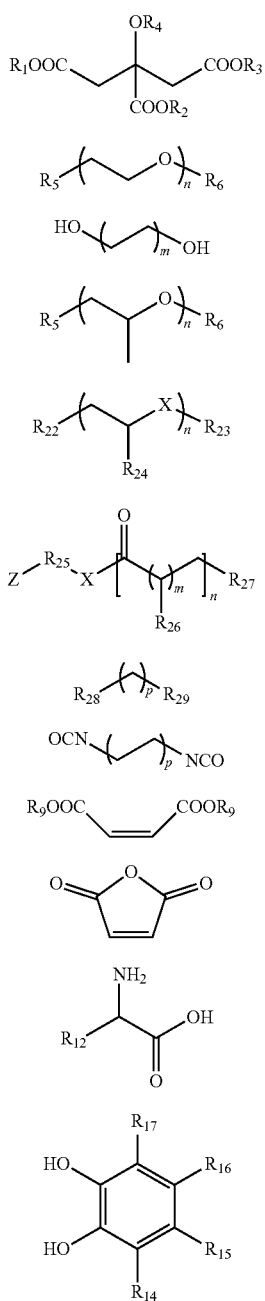

wherein $R_1$, $R_2$, and $R_3$ are each independently —H, —CH$_3$, —CH$_2$CH$_3$, or M$^+$; $R_4$ is —H or M$^+$; M$^+$ is a metal cation, e.g., a monovalent metal cation such as N$^+$ or K$^+$; $R_5$ is —H, —OH, —OCH$_3$, —OCH$_2$CH$_3$, —CH$_3$, or —CH$_2$CH$_3$; $R_6$ is —H, or a lower alkyl, such as —CH$_3$, or —CH$_2$CH$_3$; n and m are each independently integers ranging from 1 to 20 or from 1 to 100; p is an integer ranging from 1 to 20; $R_9$ is —H, —CH$_3$, or —CH$_2$CH$_3$; $R_{12}$ is an amino acid side chain; $R_{14}$, $R_{15}$, $R_{16}$, and $R_{17}$ are independently —H, —CH$_2$(CH$_2$)$_x$NH$_2$, —CH$_2$(CHR$_{18}$)NH$_2$, or —CH$_2$(CH$_2$)$_x$COOH; $R_{18}$ is —COOH or —(CH$_2$)$_y$COOH; x is an integer ranging from 0 to 20; y is an integer ranging from 1 to 20; $R_{22}$ is —H, —OH, —OCH$_3$, —OCH$_2$CH$_3$, —CH$_3$, —CH$_2$CH$_3$, —NH$_2$, NHCH$_3$, —CH$_2$CH$_2$NHCH$_3$, —N(CH$_3$)$_2$, or —CH$_2$CH$_2$N(CH$_2$CH$_3$)$_2$; $R_{23}$ is —H, —CH$_3$, or —CH$_2$CH$_3$, —(CH$_3$)$_2$, or —(CH$_2$CH$_3$)$_2$; $R_{24}$ is —H or —CH$_3$; $R_{25}$ is —(CH$_2$)$_a$—, —(CH$_2$CH$_2$O)$_b$— or —(CH$_2$OCH$_2$)$_b$—; $R_{26}$ is —H, —CH$_3$, or a C2-C20 alkyl; $R_{27}$ is —H, —C(O)CH$_3$, or —C(O)CH$_2$CH$_3$; $R_{28}$ and $R_{29}$ are independently —OH or —NH$_2$; X and Y are independently —O— or —NH—; Z is —H, —CH$_3$, —(CH$_3$)$_2$, —(CH$_2$CH$_3$)$_2$, or

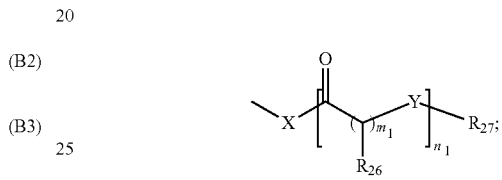

a is an integer from 0 to 20; b is an integer from 0 to 2000; n1 for the formula above is an integer between 1 and 2000; m1 and p are independently integers ranging from 1 to 20; and wherein the monomer of Formula (B4) has at least one terminus comprising —OH or —NH$_2$.

Figure 1B:
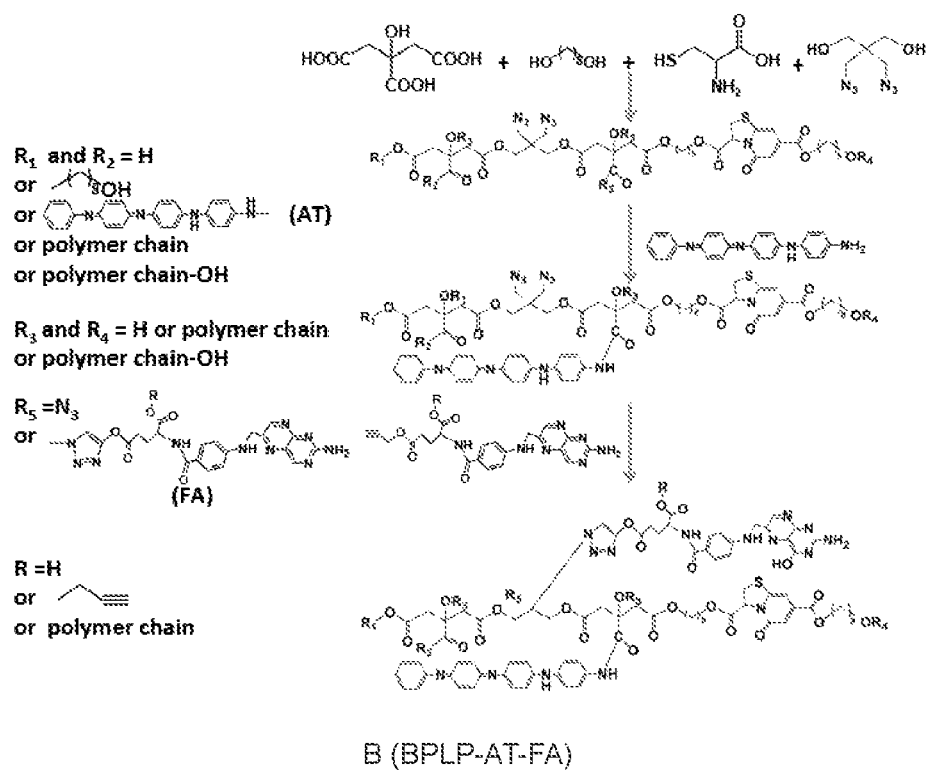
Figure 2:
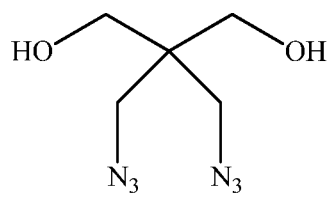
FIG. 2 shows selective examples of azide containing diols and alkyne-containing diols.
Figure 2:
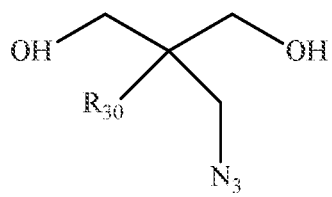
Figure 2:
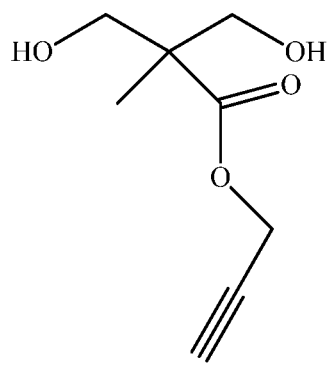
Figure 2:
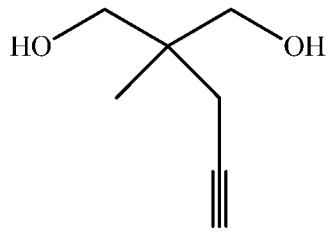
Figure 2:
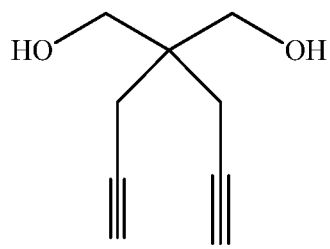
Figure 2:
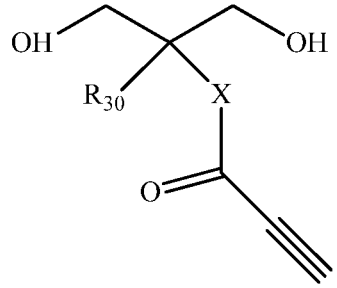
Figure 2:
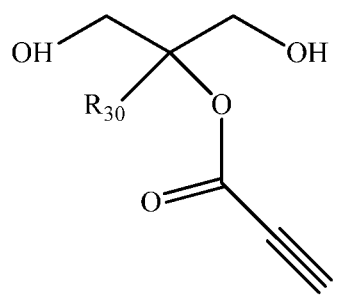
Figure 2:
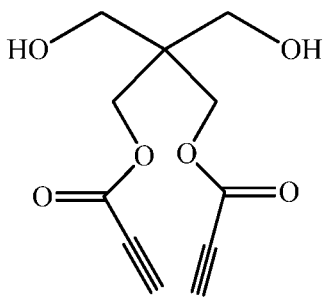

A wide variety of citrate polyesters can be made from the various monomers described above. See for example, FIGS. 1A and 1B which schematically show syntheses of biodegradable poly(octamethylene citrate) and a biodegradable photoluminescent polymer with a coupled aniline tetramer (BPLP-AT). The citrate based polyesters shown in FIGS. 1A-1B can also incorporate folate via click alkyne-azide chemistry. When citrate polyesters are synthesized without using clickable-diols, folic acid can also be conjugated to polymers via other applicable conjugation methods such as the use of water-soluble carbodiimide (WSC) for conjugation. Other useful monomers comprising one or more alkyne moieties or one or more azide moieties that can be included in the citrate polyester are shown in FIG. 2, for example.

In some embodiments, the first or second biodegradable polymer or oligomer has the structure of Formula (II):

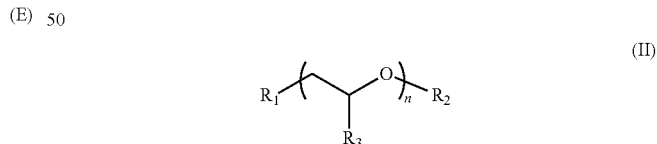

wherein $R_1$ is —OH, —NCO, or —R$_4$—NCO; $R_2$ is —H or —R$_5$—NCO; $R_3$ is —H or —CH$_3$; $R_4$ and $R_5$ are independently an alkylene, alkenylene, arylene, heteroarylene, alkoxylene, aryloxylene, or carbamate residue having 1-30 carbon atoms; and n is an integer between 10 and 1000, provided that $R_1$ and $R_2$ both provide a hydroxyl moiety or both provide an isocyanate moiety to the polymer or oligomer.

Other useful biodegradable polymers and/or oligomers that can be used to form the first or second blocks of the copolymer include diol-terminated or diisocyanate-terminated polyether or polyester such as a diol-terminated or diisocyanate-terminated poly(ethylene glycol) (PEG), poly (propylene glycol) (PPG), biodegradable photoluminescent polymer diol (BPLP), poly(vinyl alcohol) (PVA), their copolymers, poly (D. L-lactic-co-glycolic acid) (PLGA), poly (lactic acid) (PLA), polycaprolactone (PCL), polyhydroxyalkanoate (PHA), poly(lactic acid)-poly(ethylene glycol) copolymer (PLAPEG), poly(glutamic acid)-poly(ethylene glycol) copolymer (PGAPEG), PLAGACLPEG copolymer, polyhydroxybutyrate (PHB), PCLPEG, biodegradable photoluminescent polymer (BPLP), poly(ethylene glycol) maleic citrate (PEGMC), injectable citrate-based mussel-inspired bioadhesive (iCMBA), poly(octamethylene citrate) (POC), Clickable POC (POC-click) or citrate-based polymers, or a combination thereof.

The first blocks and second blocks can be linked via urethane bonds through a coupling reaction between aliphatic polyester diols and diisocyanate-terminated hydrophilic polyether segments such as PEG, PPG, or between aliphatic polyether diols and diisocyanate-terminated aliphatic polyester diol, or between aliphatic polyester diols and diisocyanate-terminated aliphatic polyester segments such as PLGA, PLA, PCL, PHA, POC, BPLP, iCMBA, POC-click. PEGMC, PLAPEG, PCLPEG, PGAPEG, PLAGACLPEG, PHB.

Forming urethane linkages among the first and second biodegradable polymers or oligomers can be carried out either in bulk or in organic solvents and typically is performed under an inert atmosphere with the exclusion of moisture. Tin catalysts such as tin(II) 2-ethylhexanoate (SnOct$_2$), ditin butyldilaurate are typically used for the reaction. Hydroxyl group and isocyanate group should typically be equal molar ratio. The reaction conditions are typically at 30-100° C. for 8-72 h.

The biodegradable block polyurethane copolymers can be crosslinked by heating the block copolymer including a citrate ester. Advantageously, prior to crosslinking, the block copolymer can be formed into a desired shape from a solution or suspension and then dried with heat to form the crosslinked biodegradable block polyurethane copolymers comprising the first and second set of blocks. The biodegradable block polyurethane copolymers can also be additionally crosslinked with the aid of initiators such as photoinitiators or redox initiators when POMC, PEGMC, or double-bond containing citrate polymer blocks are used in PU syntheses, or sodium meta periodate or silver nitrates when iCMBA blocks are used in PU syntheses, or copper catalysts used in click chemistry when clickable citrate polymers such as POC-click blocks are used in PU syntheses.

The biodegradable block polyurethane copolymers can be further functionalized when functional crosslinkable blocks are used such as POC-click, POC, urethane-doped POC, iCMBA, and biodegradable photoluminescent polymer (BPLP) are utilized during the synthesis, thus creating a versatile class of crosslinked polymers. This strategy enables additional control of material properties and functionalities leading to even more product applications within the biomedical field as well as other non-medical applications. In addition to the tunable physical properties such as mechanical properties and degradation, the functionalities added to PU due to the use of citrate polymers include but not limited to anti-inflammatory, antioxidant, anti-thrombotic, bioadhesive, and fluorescent properties, and other functionality due to the added or conjugated molecules such as folic acid.

For example, folic acid can be incorporated into the crosslinked biodegradable block polyurethane copolymers. It is believed that folic acid induces regenerative and neuroprotective effects. Locally delivered folic acid was found to be effective in inducing neuronal differentiation and increasing proliferation of neural stem cells (NSCs). The incorporation of folic acid provides the crosslinked biodegradable block polyurethane copolymers of the present disclosure with a neurotropic factor that can promote neural stem cell differentiation and neural tissue regeneration.

Moreover physically or covalently incorporating folic acid into the crosslinked biodegradable block polyurethane copolymers of the present disclosure enables designs that specifically enhance PNS regeneration. Adding a functional local folic acid delivery via the NGC itself is a novel tissue engineering strategy to promote repair of the injured brain, spinal cord, and other tissue through modification of the methylation milieu.

Figure 3:
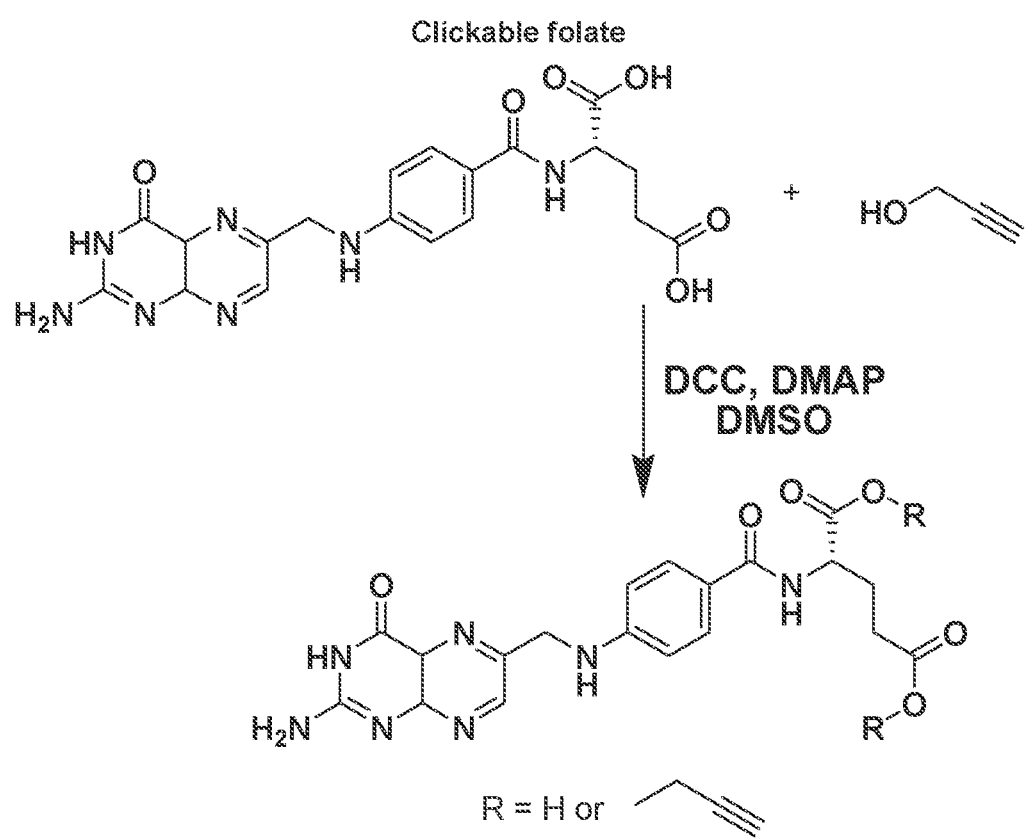
FIG. 3 shows synthesis scheme of folic acid-alkyne via click chemistry.

Folic acid can be incorporated physically into the crosslinked biodegradable block polyurethane copolymers of the present disclosure, e.g., by admixing folic acid with the biodegradable block polyurethane copolymers prior to crosslinking or thereafter. Alternatively, folic acid can be incorporated covalently into the crosslinked biodegradable block polyurethane copolymers of the present disclosure by covalent boding the folate through the use of click chemistry to form a folate pending group. FIG. 2 shows selective examples of azide containing diols and alkyne-containing diols that can be used in preparing a citrate ester and to covalently incorporate folic acid into crosslinked biodegradable block polyurethane copolymers of the present disclosure. FIG. 3 shows a representative synthesis scheme of modifying folic acid with an alkyne. Once modified with the alkyne, the folic acid can be incorporated into the crosslinked biodegradable block polyurethane copolymers by reacting with an azide on the block copolymer, i.e., representative click chemistry, to form a folate pending group as show, for example, in FIG. 1.

Various medical devices can be fabricated from the crosslinked biodegradable block polyurethane copolymers of the present disclosure including nerve repair conduits, tissue scaffolds tarsal and wound dressings, cellular ingrowth, cartilage reconstruction, organ replacement and repair, ligament and tendon repair, bone reconstruction and repair, skin reconstruction and repair, vascular graft, and coronary stents, other soft and hard tissue regeneration and implantable medical devices can also be made from the biomaterials.

In addition, the block copolymers of the present disclosure can be composited with other inorganic or metallic materials such as hydroxyapatite, calcium phosphate, bioglass, magnesium oxide, calcium oxide, carbon nanotube, graphene, etc., to form composite materials for orthopedic applications and other biomedical applications.

Advantageously, the crosslinked biodegradable block polyurethane copolymers of the present disclosure can be fabricated as a luminal structure with highly kink-resistant properties that allow for flexing of up to 140 degrees of flexion without internal collapse of the lumen.

In an aspect of the present disclosure, a nerve growth conduit is formed from one or more crosslinked biodegradable block polyurethane copolymers of the present disclosure. In an embodiment of the present disclosure, the nerve growth conduit has a core-shell or lumen-exterior scaffold structure comprising a core or lumen component having a first porosity and a shell or exterior scaffold component surrounding the core or lumen component and having a second porosity, the second porosity differing from the first porosity. The core component exhibits a higher porosity than the shell component.

Figure 4:
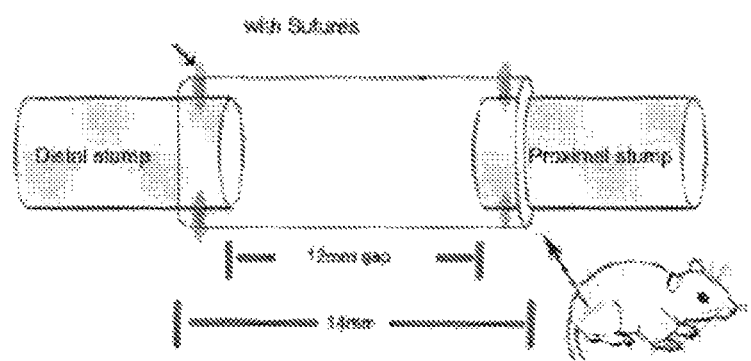
FIG. 4 shows the schematic illustration of nerve repair microsurgery. This figure is consistent with the embodiment of Example 3.

FIG. 4 shows a schematic illustration of nerve repair microsurgery. As shown in the figure, the nerve conduit, e.g., a porous nerve conduit, has a proximal end attached to a proximal stump nerve, a distal end attached to a distal stump nerve, and a central region between the proximal end and the distal end. The NGCs can be single channeled with channeled diameters from 0.5 mm to 5 mm or multi-channeled with channeled diameters from 50 microns to 500 microns. For multi-channeled NGCs, the number of channels can range from 1 to 30. For hollow porous NGCs, the pore size of NGC wall can vary from 0 nm to 500 microns (preferably less than 50 microns), the wall thickness can vary from 100 microns to 2 mm. In some embodiments, the nerve conduit can be fabricated in such a manner to create a gradient porosity from exterior (starting from 0%) to an interior region (up to 99%).

The pore size can be uniform throughout the scaffold ranging from 500 nm to 50 microns. Alternatively and as show in the embodiment of FIG. 5, the pore size can be gradient from exterior pore size of ranging from 0 nm-500 microns to lumen pore size ranging from 0 nm up to 500 microns. The wall thickness can range from 100 microns up to 2 mm.

Figure 6:
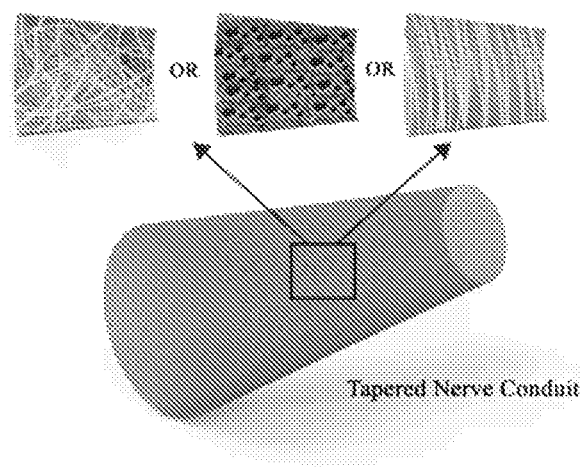
FIG. 6 shows a perspective view of a nerve growth conduit according to one embodiment described herein.

In addition or in an alternative, the nerve conduit can have a tapered tubular structure or form as illustrated in the embodiment of FIG. 6. As shown, an inner and/or outer diameter of the tubular nerve conduit can vary from a proximal end to a distal end of the nerve conduit, including in a generally continuous manner (as opposed to an undulating manner or a "ridge-and-valley" manner), such that the conduit has a larger inner and/or outer diameter at one end compared to the other end. Such a structure may be particular advantageous for nerves that taper as they proceed distally.

Figure 7:
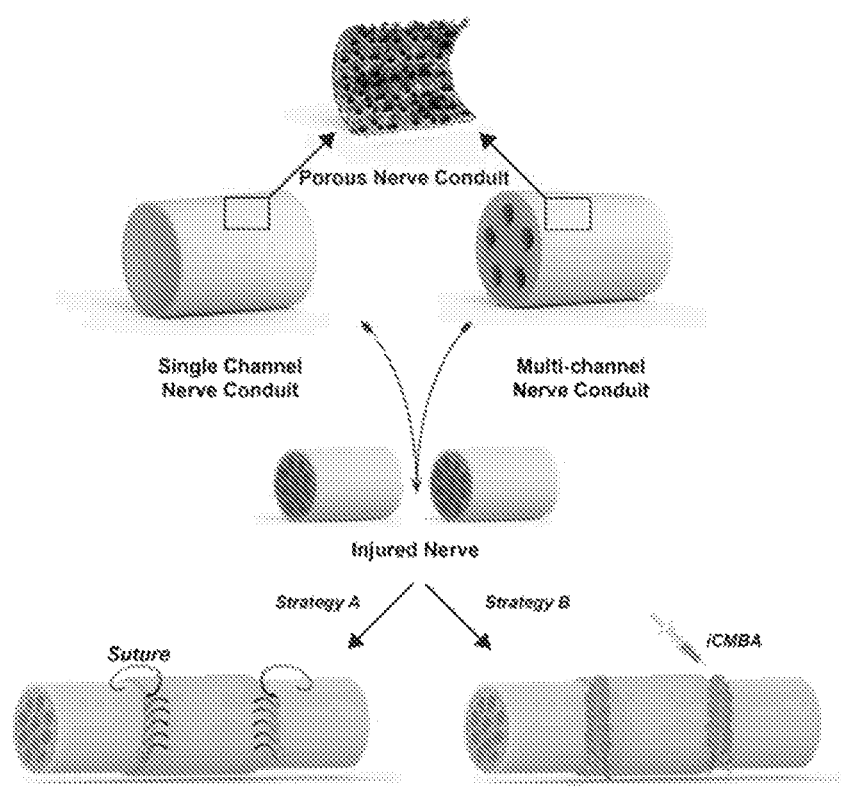
FIG. 7 shows schematic representation of fabrication and grafting of NGCs. This figure is consistent with the embodiment of Example 24.

FIG. 7 is a schematic representation of fabricating and grafting of NGCs. As shown in the embodiment of FIG. 7. NGCs can be either sutured to nerve stumps or glued to the nerve ends. For multi-channeled NGCs, both ends of the NGCs can be specifically designed as non-channeled to facilitate encasing the nerve ends through either suturing and gluing. The non-channeled portions should be at least larger or equal to the size of nerves to be bridged and can be as long as needed for securing the nerve ends. For sutureless NGC grafting, the end sections (non-channeled if it is multi-channeled NGC) of the NGCs will be immersed in or filled with a bioglue/bioadhesive to allow the glues/adhesives to be coated/absorbed in the end portion of NGCs. The nerve ends will also be coated with bioglues/bioadhesives such as iCMBA, fibrin glue, cyanoacrylate. PEG, albumin, or chitosan based bioglues or sealants or any other bioglues/adhesives/sealants used for surgery.

In an embodiment of the present disclosure, crosslinked biodegradable block polyurethane copolymers can be fabricated as nerve conduits that have a degradation rate that varies as a function of location. That is, the nerve conduit has a degradation rate that varies as a function of location within the nerve conduit.

In certain embodiments, the medical device is formed from one or more crosslinked biodegradable block polyurethane copolymers of the present disclosure incorporating folic acid. e.g., either physically or covalently. Such a medical device can locally deliver folic acid to a site of injury such as a PNS injury site. Hence, an aspect of the present disclosure includes methods for delivering folic acid to an injury site to treat or repair an injury, e.g., a PNS injury, or wound or repair tissue such as a tarsus repair by disposing a medical device formed from one or more crosslinked biodegradable block polyurethane copolymers of the present disclosure incorporating folic acid.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Example 1

Example of Synthesis of PEG-Diisocyanate Prepolymer

Diisocyanate-terminated PEG was synthesized according to Schouten et. al., Biomaterials 2005, 26, 4219-4228 with some modifications. Briefly, 2.4 g PEG ($M_n$=400, $6 \times 10^{-3}$ mol) and 0.06 g stannous octanoate were dissolved in 30 mL anhydrous 1,2-dichlorethane in a 100 mL two-necked flask at 100° C. Then, trace water in the system was removed through azeotropic distillation until roughly 15 mL of 1,2-dichloroethane were left in the flask. The remaining 15 mL of solution was transferred into a 20 mL syringe. This solution was added dropwise into a 250 mL three-necked flask inside of which 2.0 g HDI ($12 \times 10^{-3}$ mol) and 20 mL 1,2-dichloroethane were placed in advance. The reaction was carried out at 50° C. for 5 h under a nitrogen gas. The remaining PEG-diisocyanate was kept in the flask for further use.

Example 2

Example of Synthesis of PCL and PEG Based Alternating Block Polyurethanes (PUCL-Alt-PEG)

Amount 0.006 mol PCL-diol was dissolved in 60 mL 1,2-dichloroethane in a 100 mL three-neck flask. The moisture was removed by azeotropic distillation at 105° C. The remaining solution of about 20 mL was transferred into a 25 mL injector and was dropped slowly into the flask of PEG-diisocyanate prepared in Example 1. After a 48 h reaction at 75° C., the viscous solution product was cooled to room temperature and allowed to precipitate in a mixture of petroleum ether and methanol (20/1, v/v %). The product was collected and dried under vacuum to a constant weight at 40° C. The average yield was 90%. The full synthetic procedure is illustrated in the scheme below.

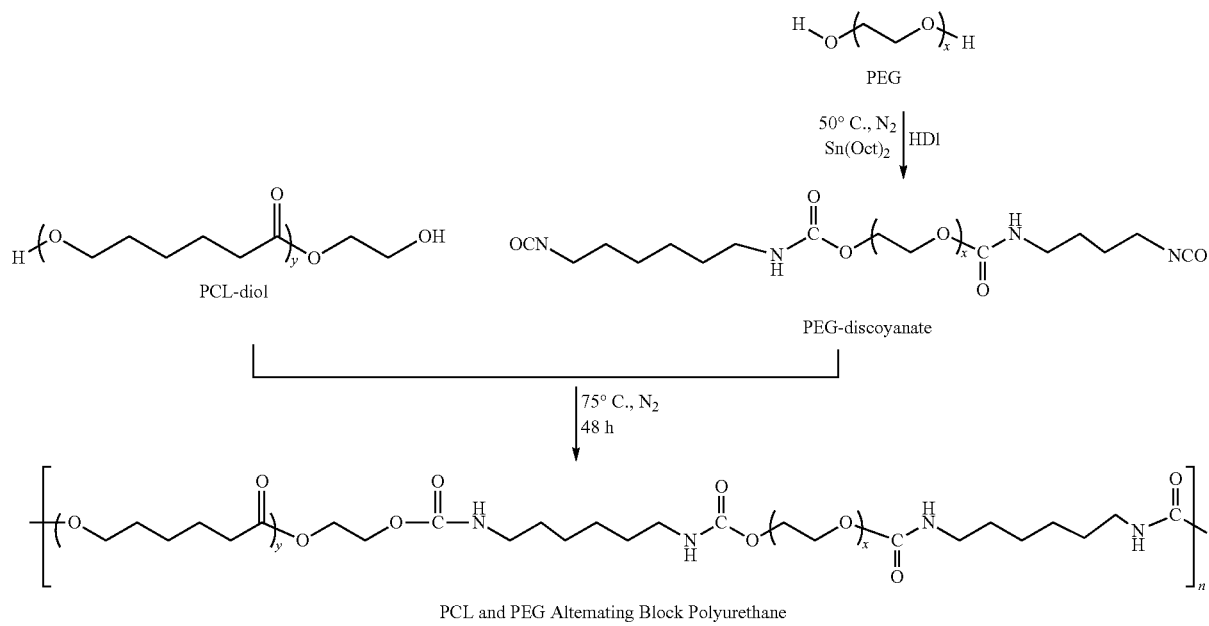

Example 3

Nerve Repair Test
Fabrication of Polyurethane Nerve Guidance Conduit

A porous polyurethane nerve guidance conduit was prepared using a dip-coating and salt-leaching method. Typically, 1 g of bock copolymer (before crosslinking) was dissolved in 10 mL N, N-dimethyl Formamide (DMF) at 60° C. for 1 h. Then 2 g of NaCl particles (5-10 μm), as a porogen for porous conduit fabrication, were added into the solution and thoroughly mixed. A stainless steel wire with an outer diameter of 1.5 mm was used as a mold. The mold was immersed in above salt suspension for 15 s and then taken out for solvent evaporation for 3 min. The above dip coating and drying cycles were repeated 5 times or more as needed to obtain desired coating thickness. After the last coating, the mold with the coating slurry was rolled on a clean white paper or on a Teflon sheet to tighten the packing of the coatings on the mold. The resulting polymer/salt coatings were then subject to air-drying for 2 days, vacuum-drying for 2 days, followed by with/without crosslinking and then salt-leaching in deionized water, freeze-drying, and demolding to obtain a porous nerve guidance conduit.

Example 4

Example of preparation of folic acid containing PCL and PEG based alternating block polyurethanes (FPUCL-alt-PEG, or FAltPU)

Five gram of PUCL-alt-PEG prepared in example 2 was dissolved in 20 mL DMF to make clear solution. Various amount of folic acid (0.1 mg to 1000 mg) was dissolved in 10 mL DMF to make another solution. The two solutions were mixed homogeneously and dried naturally. A film of PUCL-alt-PEG containing folic acid was prepared. Alternative, AltPU scaffold was prepared as described above. Various amount of folic acid (0.1 mg/L to 1000 mg/L) was dissolved in deionized (DI) water or PBS. FAltPU scaffolds were obtained by immersing the scaffolds in the above FA solution for 24 hours followed freeze-drying.

Example 5

Example of Synthesis of Poly(Lactic Acid-Co-Glycolic Acid) (PLGA) Diol

PLGA-diol was prepared by transesterification between purified PLGA and 1,4-butanediol using anhydrous toluene-p-sulfonic acid as catalyst. Typically, PLGA (5 g; MW $5\times10^4$) was dissolved in 100 mL chloroform and refluxed for 30 min following by adding toluene-p-sulfonic acid (1.5 g) and 1,4-butanediol (5 g). The reaction was carried out under reflux at 75° C. for 18 h and cooled to room temperature. Resultant solution was washed with distilled water for 4 times in order to remove the unreacted 1,4-butanediol and catalyst, then concentrated and dried under reduced pressure. The product was dried under vacuum to constant weight. The average yield was about 80%. PLGA-diol with molecular weight 2000 was obtained.

Example 6

Example of Synthesis of Poly(Octamethylene Citrate) (POC) Prepolymer and POC-Based Crosslinked Polyurethane (XAltPU-POC)

POC-diol prepolymer was synthesized according to J. Yang et al. (Synthesis and evaluation of poly(diol citrate) biodegradable elastomers. Biomaterials. 2006:27:1889-98). Briefly, citric acid and 1,8-octanediol, with a molar ratio of 1:1.1, were bulk polymerized in a three-necked reaction flask, fitted with an inlet and outlet adapter, at 160-165° C. Once the mixture had melted, the temperature was lowered to 140° C., and the reaction mixture was stirred for another 60 min to create the POC prepolymer. The prepolymer was purified by drop wise precipitation in deionized water. The precipitated pre-polymer was collected and lyophilized to obtain the purified POC-diol prepolymer. The average molecular weight of POC-diol was characterized as 850-1200 Dalton by MALDI-MS. Crosslinked polyurethanes were prepared by chain extension of the POC-diol prepolymer via urethane linkage from the primary terminal hydroxyl groups. The side tertiary hydroxyl group of the POC-diol was utilized for further thermal crosslinking to obtain POC-based crosslinked polyurethane elastomers (XPU-POC).

Example 7

Example of Synthesis of Poly(Octamethylene Citrate) (POC) and PEG Based Alternating Block Polyurethanes (PUPOC-Alt-PEG).

POC-diol 5.1 g (0.006 mol) prepared in Example 6 was dissolved in 60 mL 1,2-dichlorethane or 1,4-dioxane in a 250 ml three-neck flask. The moisture was removed by azeotropic distillation at 105° C. The remaining solution of about 20 mL was transferred into a 30 mL injector and was dropped slowly into the flask of PEG-diisocyanate prepared in Example 1. After 48 h reaction at 75° C., the viscous solution product was cooled to room temperature and allowed to precipitate in a mixture of petroleum ether and methanol (20/1, v/v %). The product was collected and dried under vacuum to a constant weight at 40° C. The average yield was 90%.

Example 8

Example of Synthesis of POC and PEG Based Crosslinked Alternating Block Polyurethane (XPUPOC-Alt-PEG)

The poly(1,8-octanediol citrate) (POC) and PEG based alternating block polyurethanes (PUPOC-alt-PEG) solution synthesized in Example 7 was cast onto a Teflon mold and allowed to dry in a chemical hood equipped with a laminar airflow until all the solvents had evaporated. The resulting PUPOC-alt-PEG film was moved into an oven maintained at 80° C. for pre-determined time periods to obtain crosslinked alternating block polyurethane doped POC polyester elastomers (XPUPOC-alt-PEG).

Example 9

Example of Synthesis of POC and PEG Based Random Block Polyurethanes (PUPOC-Ran-PEG) and Crosslinked Random Block Polyurethanes (XPUPOC-Ran-PEG)

Typically, 0.01 mol POC-diol, 0.01 mol PEG and 0.15 g stannous octanoate dissolved in 100 mL 1,2-dichloroethane or 1,4-dioxane in a 250 mL three-neck flask and water was removed by zeotropic distillation with 50 mL solution remained in the flask. When the flask was cooled to 75° C., 0.02 mol HDI in 10 mL 1,2-dichloroethane or 1,4-dioxane was injected in. The reaction mixture was stirred at 75° C. under a nitrogen atmosphere for 48 h. The viscous solution product was cooled to room temperature and allowed to precipitate in a mixture of petroleum ether and methanol (20/1, v/v %). The product was collected and dried under vacuum to a constant weight at 40° C. The average yield was 90%. The resulting PUPOC-ran-PEG film was moved into an oven maintained at 80° C. for pre-determined time periods to obtain crosslinked alternating block polyurethane doped POC polyester elastomers (XPUPOC-ran-PEG).

Example 10

Example of Synthesis of Aliphatic Biodegradable Photoluminescent Polymer Diol (BPLP-Diol) Prepolymer BPLP-diol prepolymer was synthesized according to J. Yang et al. (Development of aliphatic biodegradable photoluminescent polymers. Proceedings of the National Academy of Sciences of the United States of America. 2009:106:10086-91). Briefly, citric acid and 1,8-octanediol, with a monomer molar ratio of 1:1.1, were combined and stirred with additional L-cysteine (or other amine-containing molecules) at molar ratio of L-cysteine/citric acid 0.2. After melting at 160° C. for 20 min, the temperature was brought down to 140° C. stirring continuously for another 75 min to obtain the BPLP-cysteine (BPLP-Cys) diol prepolymer. The BPLP-diol prepolymer was purified by precipitating prepolymer solution in water followed by freeze-drying. The average molecular weight of BPLP-diol was characterized as 800 by MALDI-MS. BPLP-based polyurethanes (PU-BPLP) were prepared by chain extension of the BPLP-diol prepolymer via urethane linkages from the primary terminal hydroxyl groups. The side tertiary hydroxyl group of the BPLP-diol was utilized for further thermal crosslinking to obtain BPLP-based crosslinked polyurethane elastomers (XPU-BPLP).

Example 11

Example of Synthesis of Aliphatic Biodegradable Photoluminescent Polymer Diol (BPLP-Diol) and PEG Based Alternating Block Polyurethanes (PUBPLP-Alt-PEG)

BPLP-diol 5.0 g (0.006 mol) prepared in Example 10 was dissolved in 60 mL 1,2-dichlorethane in a 250 ml three-neck flask. The moisture was removed by azeotropic distillation at 105° C. The remaining solution of about 20 mL was transferred into a 30 mL injector and was dropped slowly into the flask of PEG-diisocyanate prepared in Example 1. After 48 h reaction at 75° C., the viscous solution product was cooled to room temperature and allowed to precipitate in a mixture of petroleum ether and methanol (20/1, v/v %). The product was collected and dried under vacuum to a constant weight at 40° C. The average yield was 90%.

Example 12

Example of Synthesis of BPLP and PEG-Based Crosslinked Alternating Block Polyurethane Doped BPLP Polyester Elastomers (XPUBPLP-Alt-PEG)

The BPLP-diol and PEG based alternating block polyurethanes (PUBPLP-alt-PEG) solution synthesized in Example 10 was cast into a Teflon mold and allowed to dry in a chemical hood equipped with a laminar airflow until all the solvents had evaporated. The resulting PUBPLP-alt-PEG film was moved into an oven maintained for post polymerization at 80° C. for 4 days to obtain crosslinked alternating block polyurethane doped BPLP polyester elastomers (XPUBPLP-alt-PEG).

Example 13

Example of Synthesis of Aliphatic BPLP and PEG Based Random Block Polyurethanes (PUBPLP-Ran-PEG)

Typically, 0.01 mol POC-diol, 0.01 mol PEG and 0.15 g stannous octanoate dissolved in 100 mL 1,2-dichloroethane in a 250 mL three-neck flask and water was removed by zeotropic distillation with 50 mL solution remained in the flask. When the flask was cooled to 75° C., 0.02 mol HDI in 10 mL 1,2-dichloroethane was injected in. The reaction mixture was stirred at 75° C. under a nitrogen atmosphere for 48 h. The viscous solution product was cooled to room temperature and allowed to precipitate in a mixture of petroleum ether and methanol (20/1, v/v %). The product was collected and dried under vacuum to a constant weight at 40° C. The average yield was 90%.

Example 14

Example of Synthesis of Citrate-Based Mussel-Inspired Bioadhesive (CMBA)-Diol

The CMBA-diol prepolymer was synthesized according to M. Mehdizadeh et al. (Injectable citrate-based mussel-inspired tissue bioadhesives with high wet strength for sutureless wound closure. Biomaterials. 2012; 33:7972-83) with some modifications. Briefly, citric acid and 1,8-ocatnediol, with a monomer molar ratio of 1:1.1 and melt at 160° C. for 20 min. Next, under nitrogen gas flow, a calculated amount of dopamine was added to the mixture. After allowing enough time for a clear solution to form, the temperature was brought down to 140° C. under vacuum and stirring for the required time until the desired molecular weight was achieved. The resulting iCMBA-diol prepolymers were dissolved in 1,2-dicholoethane or 1,4-dioxane. The iCMBA-prepolymer was purified by precipitating from 1,2-dicholoethane or 1,4-dioxane solution in water followed by freeze drying.

Example of Synthesis of Citrate-Based Mussel-Inspired Bioadhesive (CMBA) Based Polyurethanes (PU-CMBA) and Crosslinked PU-CMBA.

The CMBA-diol prepolymer was synthesized according to M. Mehdizadeh et. al., [43] with some modifications. Briefly, citric acid and 1,8-ocatnediol, with a monomer molar ratio of 1:1.1 and melt at 160° C. for 20 min. Next, under nitrogen gas flow, a calculated amount of dopamine was added to the mixture. After allowing enough time for a clear solution to form, the temperature was brought down to 140° C. under vacuum and stirring for the required time until the desired molecular weight was achieved. The resulting iCMBA-prepolymers were dissolved in 1,2-dicholoethane or 1,4-dioxane. The iCMBA-prepolymer was purified by precipitating from 1,2-dicholoethane or 1,4-dioxane solution in water followed by freeze-drying. The crosslinked XPU-CMBA was prepared with procedures similar to Example 6.

Example of Synthesis of Citrate-Based Mussel-Inspired Bioadhesive (CMBA) and PEG Based Alternating Polyurethanes (PUCMBA-Alt-PEG) and Crosslinked PUCMBA-Alt-PEG (XPUCMBA-Alt-PEG)

The CMBA-diol prepolymer was synthesized according to M. Mehdizadeh et. al., [43] with some modifications. Briefly, citric acid and 1,8-ocatnediol, with a monomer molar ratio of 1:1.1 and melt at 160° C. for 20 min. Next, under nitrogen gas flow, a calculated amount of dopamine was added to the mixture. After allowing enough time for a clear solution to form, the temperature was brought down to 140° C. under vacuum and stirring for the required time until the desired molecular weight was achieved. The resulting iCMBA-prepolymers were dissolved in 1,2-dicholoethane or 1,4-dioxane. The iCMBA-prepolymer was purified by precipitating from 1,2-dicholoethane or 1,4-dioxane solution in water followed by freeze-drying.

For (PUCMBA-alt-PEG) synthesis, typically, 0.01 mol CMBA-diol and 0.15 g stannous octanoate dissolved in 100 mL 1,2-dichloroethane in a 250 mL three-neck flask and water was removed by zeotropic distillation with 50 mL solution remained in the flask. When the flask was cooled down, it was injected into the 0.01 mole of PEG-diisocyanate prepared in Example 1. The reaction mixture was stirred at 75° C. under a nitrogen atmosphere for 48 h. The viscous solution product was cooled to room temperature and allowed to precipitate in a mixture of petroleum ether and methanol (20/1, v/v %). The product was collected and dried under vacuum to a constant weight at 40° C. The average yield was 90%. The XPUCMBA-alt-PEG was prepared with procedures similar to Example 12.

Example 15

Example of Synthesis of PCL-Based Clickable Random Block Polyurethane with Azide Group (RanPU-N3)

Amount 0.003 mol PCL-diol was dissolved in 50 mL 1,2-dichloroethane in a 100 mL three-neck flask. The moisture was removed by azeotropic distillation at 105° C. The remaining solution of about 20 mL was transferred into a 25 mL injector and was dropped slowly into the flask of PEG-diisocyanate (0.006 mol) prepared in Example 1 along with 0.003 mole of 2,2-bis(azidomethyl) propane-1,3-diol (Prepared according to Jian Yang et. al, Advanced Materials 2014, 26, 1906-1911) in 5 mL 1,2-dichloroethane. The reaction was allowed for another 48 h at 75° C., the viscous solution product was cooled to room temperature and allowed for further click reaction.

Example 16

Example of Synthesis of Clickable Random Block Polyurethane with Alkyne Group (RanPU-Al)

Amount 0.003 mol of PCL-diol was dissolved in 50 mL 1,2-dichloroethane in a 100 mL three-neck flask. The moisture was removed by azeotropic distillation at 105° C. The remaining solution of about 20 mL was transferred into a 25 mL injector and was dropped slowly into the flask of PEG-diisocyanate (0.006 mol) prepared in Example 1 along with 0.003 mole of propargyl 2,2-bis(hydroxylmethyl)propionate (alkyne-diol) prepared as described in J Yang et al. [45] in 5 mL 1,2-dichloroethane. The reaction was allowed for another 48 h at 75° C.

Example 17

Example of Synthesis of Crosslinked Random Block Polyurethane Via Click Chemistry (XRanPU-Click)

It is considered favorable to synthesize biomaterials without using any potentially toxic metal ions. The copper-catalyzed click reaction of azide and alkyne is thus not the choice for this preparation although it is can be used. Herein, thermal synchronous binary (TSB) cross-linked click chemistry was formed by heating the mixture of RanPU-N3 and RanPU-Al at 100° C. for 3 days. Therefore, equal amount of RanPU-N3 (Example 15) and RanPU-Al (Example 16) dissolved in 1,2-dicholoethane to prepare the film. The film was heated at 100° C. for 3 days under vacuum to obtain the crosslinked alternating block polyurethane (XRanPU-click).

Example 18

Example of Synthesis of PCL and PEG-Based Clickable Alternating Block Polyurethane with Azide Group (AltPU-N3).

Amount 0.003 mol PCL-diol was dissolved in 50 mL 1,2-dichloroethane in a 100 mL three-neck flask. The moisture was removed by azeotropic distillation at 105° C. The remaining solution of about 20 mL was transferred into a 25 mL injector and was dropped slowly into the flask of PEG-diisocyanate (0.006 mol) prepared in Example 1 and react for 24 h at 75° C. to obtain PCL-PEG diisocyanate. Next, 0.003 mole of 2,2-bis(azidomethyl) propane-1,3-diol prepared according to Jian Yang et. al. (Click chemistry plays a dual role in biodegradable polymer design. Adv Mater. 2014:26:1906-11) in 5 mL 1,2-dichloroethane was added to the above PCL-PEG diisocyanate solution. The reaction was allowed for another 48 h at 75° C. and then the resulting viscous solution product was cooled to room temperature and allowed to precipitate in a mixture of petroleum ether and methanol (20/1, v/v %). The product was collected and dried under vacuum to a constant weight at 40° C.

Example 19

Example of Synthesis of PCL and PEG-Based Clickable Alternating Block Polyurethane with Alkyne Group (AltPU-Al).

Amount 0.003 mol PCL-diol was dissolved in 50 mL 1,2-dichloroethane in a 100 mL three-neck flask. The moisture was removed by azeotropic distillation at 105° C. The remaining solution of about 20 mL was transferred into a 25 mL injector and was dropped slowly into the flask of PEG-diisocyanate (0.006 mol) prepared in Example 1 and react for 24 h at 75° C. to obtain PCL-PEG diisocyanate. Next, 0.003 mole of propargyl 2,2-bis(hydroxylmethyl)propionate (alkyne-diol) prepared according to Jian Yang et al. (Click chemistry plays a dual role in biodegradable polymer design. Adv Mater. 2014; 26:1906-11) in 5 mL 1,2-dichloroethane was added to the above PCL-PEG diisocyanate solution. The reaction was allowed for another 48 h at 75° C. and then the resulting viscous solution product was cooled to room temperature and allowed to precipitate in a mixture of petroleum ether and methanol (20/1, v/v %). The product was collected and dried under vacuum to a constant weight at 40° C.

Example 20

Example of Synthesis of Crosslinked Alternating Block Polyurethane Via Click Chemistry (XAltPU-Click)

It is considered favorable to synthesize biomaterials without using any potentially toxic metal ions. The copper-catalyzed click reaction of azide and alkyne is thus not the choice for this preparation although it is can be used. Herein, thermal synchronous binary (TSB) cross-linked click chemistry was formed by heating the mixture of AltPU-N3 and AltPU-Al at 100° C. for 3 days. Therefore, equal amount of AltPU-N3 and AltPU-Al dissolved in 1,2-dicholoethane to prepare the film. The film was heated at 100° C. for 3 days under vacuum to obtain the crosslinked alternating block polyurethane (XRanPU-click).

Alternatively, 0.005 mol PCL-diol, 0.001 mole of alkyne-diol, and 0.006 mole of PEG-diisocyanate will be added altogether into the flask to react for 48 h at 75° C. The resultant viscous solution product was cooled to room temperature and allowed for further click reaction.

Example 21

Choices of azide-containing diols and alkyne-containing diols as shown in FIG. 2.
H1: 2,2-bis(azidomethyl)propane-1,3-diol;
H2: 2-(azidomethyl)-2-methylpropane-1,3-diol; 2-(azidomethyl)-2-ethylpropane-1,3-diol.
I1: Propargyl 2, 2-bis(hydroxyl-methyl)propionate;
I2: 2-methyl-2-(prop-2-ynyl)propane-1,3-diol;
I3: 2,2-di(prop-2-ynyl)propane-1,3-diol;
I4: R=CH3, R1=O, 1,3-dihydroxy-2-methylpropan-2-yl propiolate; R=CH2CH3, R1=O, 1-hydroxy-2-(hydroxymethyl)butan-2-yl propiolate; R=CH3, R1=NH, N-(1,3-dihydroxy-2-methylpropan-2-yl)propiolamide;
R=CH2CH3, R1=NH, N-(1-hydroxy-2-(hydroxymethyl)butan-2-yl)propiolamide
I5: R=CH3, 1,3-dihydroxy-2-methylpropan-2-yl propiolate; R=CH2CH3, 1-hydroxy-2-(hydroxymethyl)butan-2-yl propiolate:
I6: 1,3-dihydroxy-2,4-yl propiolates.

Example 22

Example of Synthesis of Alkyne-Modified Folic Acid (FA-Al) as Shown in Figure Below.

Folic acid (4.41 g, 0.01 mol) and excess propargyl alcohol (0.866 mL, 1.5 eq.) were dissolved in DMSO (20 mL), dicyclohexyl-carbodiimide (DCC, 2.27 g, 0.011 mol) and 4-(dimethylamino)-pyridine (DMAP, 0.013 g, 0.01 eq. to DCC) were dissolved in 20 mL DMSO and added slowly in the folic acid solution in DMSO. The reaction mixture was stirred at room temperature for 24 hours, and then the precipitate was removed by filtration. The filtered solution was then precipitated out in diethyl ether and the modified folate was obtained after centrifuging and washing in diethyl ether followed by vacuum drying.

Example 23

Example of Synthesis of Folic Acid-Containing Polyurethane Via Click Chemistry.

RanPU-N3 in Example 15 and AltPU-N3 in Example 18 can be reacted with FA-Al to form RanPU-FA and AltPU-FA via click chemistry. The molar ratios between AltPU-N3 and FA-Al can be varied from 1/0.1 to 1/1.

The FA-Al (Example 22) can be reacted with any above azide-containing PU via click chemistry.

Example 24

Strategies for Nerve Guidance Conduit (NGC) Fabrication and Grafting

Porous NGCs were made as in Example 3. Multi-channeled NGCs can be made as described in our previous publication. (Fabrication and characterization of biomimetic multichanneled crosslinked-urethane-doped polyester tissue engineered nerve guides. J Biomed Mater Res A. 2013). As shown in FIG. 7. For hollow porous NGCs, the pore size of NGC wall can vary from 0 nm to 500 microns (ideally less than 50 microns), the wall thickness can vary from 100 microns to 2 mm. NGCs can be either sutured to nerve stumps or glued to the nerve ends. For multi-channeled NGCs, both ends of the NGCs were specifically designed as non-channeled to facilitate encasing the nerve ends through either suturing and gluing. The non-channeled portion should be at least larger or equal to the size of nerves to be bridged and can be as long as needed for securing the nerve ends. For sutureless NGC grafting, the end sections (non-channeled if it is multi-channeled NGC) of the NGCs will be immersed in or injected with a bioglue/bioadhesive such as fibrin glue, iCMBA and any other glues to allow the glue/adhesive to be coating/absorbed in the end portion of porous scaffolds. The nerve ends will also be coated with bioglues/bioadhesives. Then the NGCs will be aligned, encased, and glued with the nerve ends.

Example 25

Figure 8:
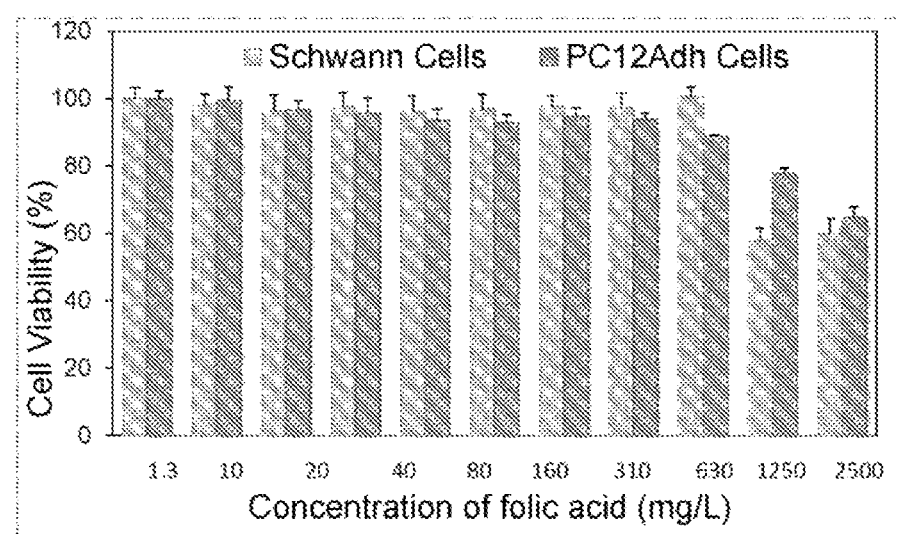
FIG. 8 shows cytotoxicity of CCK assay for Schwann cells and PC-12 cells cultured with folic acid supplemented culture medium suggesting that folic acid is not cytotoxic to both cells up to 1250 mg/L. Relative cell viability with respect to control group (1.3 mg/L folic acid in original culture medium) is plotted against increasing folic acid concentrations. Data are shown as mean±SEM; n=8; * p<0.05. This figure is consistent with the embodiment of Example 25.

Example of Schwann cells and PC-12 cells culture in folic acid-supplemented medium. Cytotoxicity of CCK assay for Schwann cells and PC-12 cells cultured with folic acid supplemented culture medium suggesting that folic acid is not cytotoxic to both cells up to 1250 mg/L (FIG. 8). The folic acid supplemented medium can promote PC-12 neurite outgrowth rate in a dose-dependent manner. Within the concentrations investigated, 50-100 mg/L folic acid supplements are optimal for promoting PC-12 differentiation and neurite outgrowth. The results showed dose-dependent neurite outgrowth activity at 3 day of culture of PC-12 cells in folic acid-supplemented neural differentiation medium that contain 5 ng/ml of neural growth factor. Highest neurite outgrowth observed with 50 mg/L folic acid.

Example 26

Figure 9:
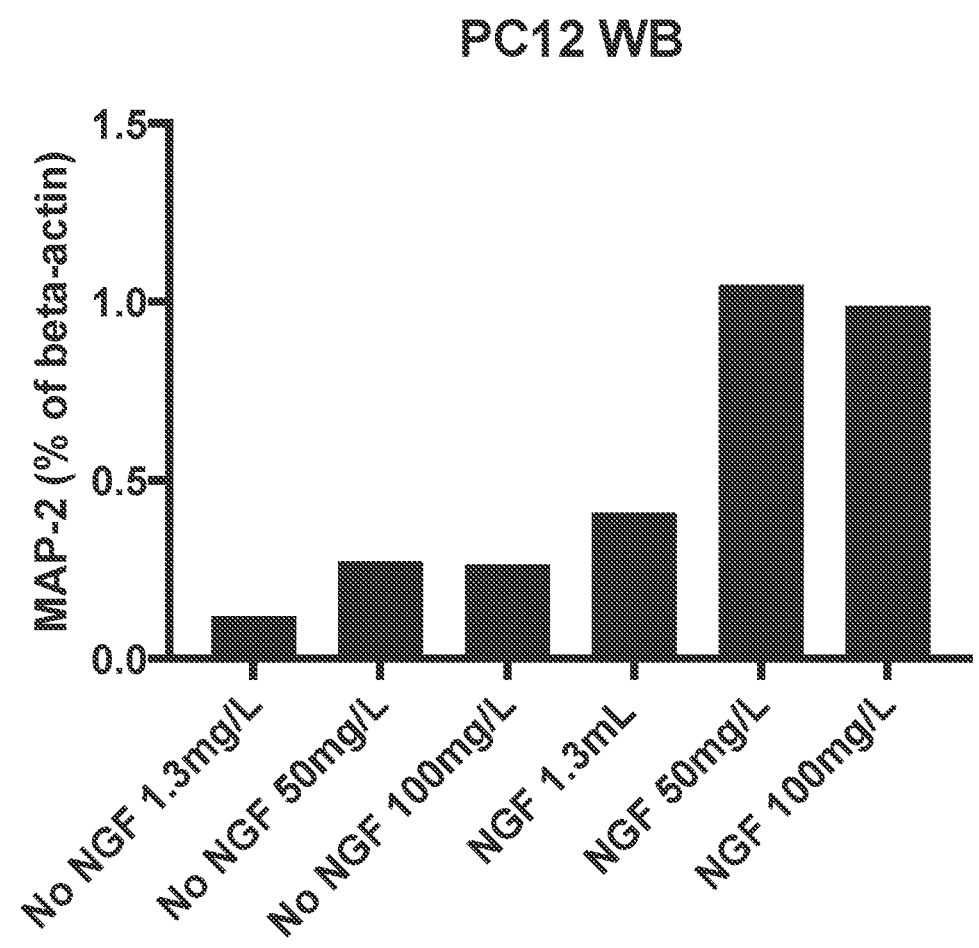
FIG. 9 is a chart showing the results of incubation of PC12 cells with media containing three concentrations of folate for 14 days in the presence or absence of NGF and the percentage of MAP-2 protein in each group with respect to beta-actin (load control).

This example investigated neurotrophic effects of folate supplemented in cell culture media on two relevant cell lines, Schwann cells (glial cells of the PNS) and PC12 cells (a cell line derived from a pheochromocytoma of the rat adrenal medulla). The cell media with folate concentrations up to 1000 mg/L supported the viability of both cells lines (cell viability>80%). The other studies conducted include 1) Schwann cell migration study, 2) PC12 cell neurite outgrowth assay, 3) western blot analysis of microtubule-associated protein-2 (MAP-2) in PC12 cells, 4) quantification of global DNA methylation in both Schwann and PC12 cells, using different concentrations of folate-fortified medium, and 5) in vivo examination of folate effects for nerve regeneration. Schwann cell migration is critical for remyelination of injured nerves so we studied the chemotactic ability of folate on facilitating Schwann cell migration using a transwell model (pore size 8 m) and microchannel-based migration assay. For the transwell model, the cells were allowed to adhere to the filter for 1 hr prior to migrating to the bottom side of the filter for 4 hr. The highest number of Schwann cells migrated toward the cell medium containing 50 mg/L folate (compared to media containing 4, 100, and 200 mg/L folate). Similarly, Schwann cell migration was monitored using live cell imaging in microchannels (width: 200 μm) connecting two reservoirs filled with media containing different concentrations of folate. Sequential phase contrast images of cells were captured every 15 mins while the cells were allowed to migrate in the channels between the left reservoir of the cell chamber filled with the low folate medium (4 mg/L) and the right reservoir filled with the high folate medium (50 mg/L). The sequential images clearly show the migration of Schwann cell from low folate medium to high folate medium. In order to determine the range of concentrations of folate that can generate the maximum axonal regeneration, we studied the effects of different concentrations of folate on improving neurite extension of PC12 cells using immunocytochemical analysis and the Image J software. Average neurite length was determined by measuring the neurites longer than twice the neuron soma diameter of at least 100 cells randomly selected from each group. Based on our findings, 50-100 mg/L folate along with 50 ng/mL NGF helped increase neurite outgrowth the most (>150 μm on day 7) compared to the control medium containing 1.3 mg/L of folate (<100 μm on day 7) and other folate concentrations. For better understanding the folate effect on PC12 differentiation, microtubule associated protein-2 (MAP-2) was quantified in PC12 cell lysates cultured in different concentrations of folate for two weeks using western blot. MAP-2 is the protein associated with the formation of neurites and dendrites at early developmental stages as a sensitive and specific marker for neurons. PC12 cells were incubated with cell media containing three concentrations of folate (1.3, 50, and 100 mg/L) for 14 days in the presence or absence of NGF (50 ng/mL). The folate medium at 50 mg/L produced 2.56 folds higher MAP-2 protein expression than the control medium (1.3 mg/L folate) in the presence of NGF. Even in the absence of NGF, folate-supplemented medium (with 50 and 100 mg/L folate) generated 2.22-2.30 folds higher MAP-2 expression compared to the control sample with 1.3 mg/L folate. FIG. 9. As folate has been considered to promote neuronal differentiation by catalyzing DNA methylation, global DNA methylation was quantified in both Schwann and PC12 cells after cultured in different folate media. Global DNA methylation was the highest at 50 mg/L folate on the second days of culturing both Schwann and PC12 cells. Further examination will be performed on this phenomenon to find out if and how global or gene-specific DNA methylation is relevant to the differentiation of glial and neuronal cells. Preliminary in vivo studies showed very exciting results of folate-fortified kink-resistant CUPE NGCs in terms of their lower autophagy, improved electrophysiology results (indicated as nerve conduction velocity or NCV), and better sciatic function index (SFI) as compared to the control CUPE and PCL NGCs, 4 weeks after surgery (2 cm sciatic nerve gaps were created in rats (180-220 g, N=26)) and implantation. Folate-CUPE (fCUPE) and folate-PCL (fPCL) NGCs were prepared by dipping NGCs in phosphate-buffered saline (PBS) containing 100 mg/L folate and freeze-drying method. The SFI values were calculated as described by Bain et al. It is also worthwhile to note that folate-CUPE NGCs showed a better SFI result and comparable NCV result as compared with autografts. These compelling in vitro and in vivo data clearly revealed folate can be used as a neurotrophic factor in NGC design for improved peripheral nerve regeneration.

Example 27

Figure 5:
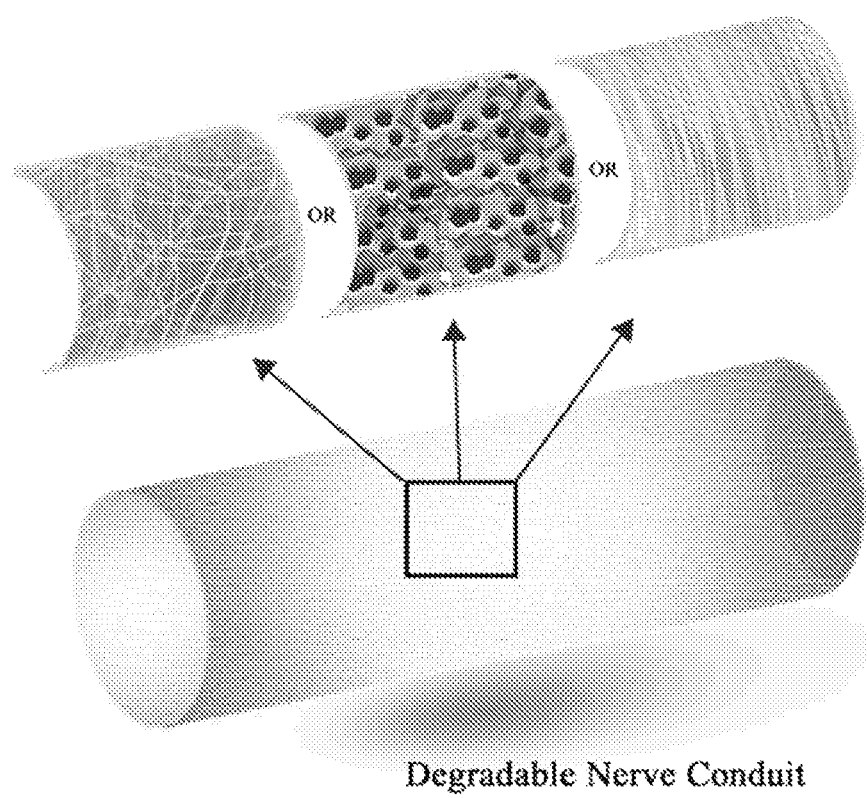
FIG. 5 shows a perspective view of a nerve growth conduit according to one embodiment described herein.

One embodiment of a nerve conduit described herein is illustrated in FIG. 5. With reference to FIG. 5, the nerve conduit is a porous nerve conduit that may be formed from a polymeric material described herein. Additionally, the porous nerve conduit has a degradation or biodegradation rate that varies as a function of location or spatial region of the nerve conduit. Specifically, in the embodiment of FIG. 5, the nerve conduit degrades more quickly at the proximal and distal ends of the nerve conduit, and more slowly in a central region of the nerve conduit. Thus, the nerve conduit exhibits a degradation rate gradient. Such a gradient can be achieved by forming the nerve conduit from a plurality of materials, the materials having different degradation rates, including in vivo. The plurality of materials can include a plurality of differing polymeric materials described hereinabove, including alternating or random block polyurethane materials. The plurality of materials may also include other materials, such as PLLA, PLGA, PCL, PVA, or collagen implant materials. In general, any materials not inconsistent with the objectives of the present disclosure may be used to form a nerve conduit having the structure described in this Example. Moreover, a nerve conduit having such a structure, in some cases, can permit the degradation profile (in both time and space) to match or correspond to a tissue growth pattern, such as a nerve tissue growth pattern. It is further to be understood that the nerve conduits can be hollow tubes or multi-channeled tubular structures.

Example 28

One embodiment of a nerve conduit described herein is illustrated in FIG. 7. With reference to FIG. 7, the nerve conduit has a tapered tubular structure or form. Thus, an inner and/or outer diameter of the tubular nerve conduit can vary from a proximal end to a distal end of the nerve conduit. More particularly, the inner and/or outer diameter of the nerve conduit can increase or decrease from the proximal end to the distal end, including in a generally continuous manner (as opposed to an undulating manner or a "ridge-and-valley" manner), such that the conduit has a larger inner and/or outer diameter at one end compared to the other end. Such a structure may be particular advantageous for nerves that taper as they proceed distally. In general, the taller an individual patient, the longer the individual's limbs, and the more tapered the distal nerves can be. Thus, the shape or form factor of a nerve conduit described herein can substantially mimic the tapered nerve tissues, thereby facilitating conduit placement and tissue regeneration.

The nerve conduits of Examples 27 and 28 can be provided with a porous structure using a particulate-leaching method or a gas-foaming method. Fibrous and porous conduits can be formed by electrospinning, melt-extrusion, or 3D printing. Moreover, for both Examples 27 and 28, the fibers of the nerve conduits can be circumferentially aligned or randomly aligned. Additionally, the fiber diameter can range from 10 nm to 2 mm.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of locally delivering folic acid to a peripheral nerve injury site, the method comprising:
    disposing a medical device at the peripheral nerve injury site, the medical device being formed from a block copolymer comprising:
        a plurality of first blocks formed from a first biodegradable polymer or oligomer;
        a plurality of second blocks formed from a second biodegradable polymer or oligomer that differs from the first polymer or oligomer; and
        folic acid,
    wherein the first blocks and second blocks are linked via urethane bonds,
    wherein the folic acid is physically or covalently incorporated into the block copolymer,
    wherein the first blocks or the second blocks comprise a citrate ester,
    wherein the first blocks and second blocks are crosslinked via the citrate ester; and
    wherein the medical device delivers the folic acid to the peripheral nerve injury site in a concentration of 4 to 200 mg/L.

2. The method of claim 1, wherein the folic acid is:
    covalently bonded to the block copolymer; or
    non-covalently entrapped within the block copolymer.

3. The method of claim 1, wherein the first or second polymer or oligomer comprises a diol-terminated or diisocyanate-terminated polyester prepared from the reaction product of (i) citric acid, a citrate, or an ester of citric acid with (ii) a polyol, wherein the citrate has the structure of Formula (I):

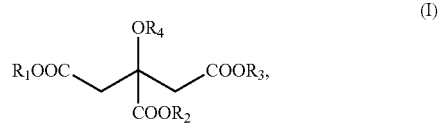

wherein $R_1$, $R_2$, and $R_3$ are independently —H, —$CH_3$, —$CH_2CH_3$, or $M^+$; $R_4$ is —H or $M^+$; and $M^+$ is a metal cation.

4. The method of claim 1, wherein the first polymer or oligomer comprises a diol-terminated aliphatic polyester, and the second polymer or oligomer comprises a diisocyanate-terminated hydrophilic polymer or oligomer.

5. The method of claim 1, wherein the first polymer or oligomer comprises a diol-terminated polyether, and the second polymer or oligomer comprises a diisocyanate-terminated aliphatic polyester.

6. The method of claim 1, wherein the first or second polymer or oligomer has the structure of Formula (I):

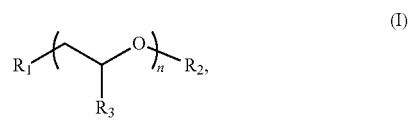

wherein $R_1$ is —OH, —NCO, or —$R_4$—NCO;
$R_2$ is —H or —$R_5$—NCO;
$R_3$ is —H or —$CH_3$;
$R_4$ and $R_5$ are independently an alkylene, alkenylene, arylene, heteroarylene, alkoxylene, aryloxylene, or carbamate residue having 1-30 carbon atoms; and
n is an integer between 10 and 1000,
provided that $R_1$ and $R_2$ both provide a hydroxyl moiety or both provide an isocyanate moiety to the polymer or oligomer.

7. The method of claim 1, wherein the first polymer or oligomer comprises a diol-terminated poly (D, L-lactic-co-glycolic acid) (PLGA), poly(lactic acid) (PLA), polycaprolactone (PCL), polyhydroxyalkanoate (PHA), poly(lactic acid)-poly(ethylene glycol) copolymer (PLAPEG), poly(glutamic acid)-poly(ethylene glycol) copolymer (PGAPEG), PLAGACLPEG copolymer, polyhydroxybutyrate (PHB), or a combination thereof.

8. The method of claim 1, wherein the second polymer or oligomer comprises a diisocyanate-terminated poly (D, L-lactic-co-glycolic acid) (PLGA), poly(lactic acid) (PLA), polycaprolactone (PCL), polyhydroxyalkanoate (PHA), poly(lactic acid)-poly(ethylene glycol) copolymer (PLAPEG), poly(glutamic acid)-poly(ethylene glycol) copolymer (PGAPEG), PLAGACLPEG copolymer, polyhydroxybutyrate (PHB), or a combination thereof.

9. The method of claim 3, wherein the polyol comprises a C2-C20 α,ω-n-alkane diol.

10. The method of claim 3, wherein the polyol comprises a poly(ethylene glycol).

11. The method of claim 3, wherein the polyol comprises a poly(propylene glycol).

12. The method of claim 3, wherein the polyester comprises the reaction product of (i) citric acid, a citrate, or an ester of citric acid with (ii) a polyol, and (iii) an amine, an amide, or an isocyanate.

13. The method of claim 12, wherein the polyester comprises the reaction product of (i) citric acid, a citrate, or an ester of citric acid with (ii) a polyol, and (iii) a diisocyanate.

* * * * *